United States Patent [19]

Tateiwa

[11] Patent Number: 5,444,529
[45] Date of Patent: Aug. 22, 1995

[54] METHOD OF INSPECTING PARTICLES ON SEMICONDUCTOR DEVICES

[75] Inventor: Kenji Tateiwa, Neyagawa, Japan

[73] Assignee: Matsushita Electric Industrial Co., Ltd., Kadoma, Japan

[21] Appl. No.: 334,801

[22] Filed: Nov. 4, 1994

Related U.S. Application Data

[63] Continuation of Ser. No. 36,199, Mar. 23, 1993, abandoned.

[30] Foreign Application Priority Data

Jun. 8, 1992 [JP] Japan .................. 4-147167

[51] Int. Cl.6 ................................................ G01B 9/02
[52] U.S. Cl. .................................... 356/337; 356/237
[58] Field of Search ................ 356/337, 338, 237

[56] References Cited

U.S. PATENT DOCUMENTS 4,073,975 2/1978 Buckwalter et al. ............... 427/170
5,061,068 10/1991 Menon .................................. 356/237

FOREIGN PATENT DOCUMENTS 62-66139 3/1987 Japan .
62-220842 9/1987 Japan .
2-216035 8/1990 Japan .

Primary Examiner—Robert P. Limanek
Assistant Examiner—David B. Hardy
Attorney, Agent, or Firm—Ratner & Prestia

[57] ABSTRACT

Liquid water drops are formed around particles situated on a substrate and diffuse laser light patterns are intensified by the liquid water drops to make it possible to detect minute particles of 0.1 μm and less in dimension.

12 Claims, 3 Drawing Sheets

METHOD OF INSPECTING PARTICLES ON SEMICONDUCTOR DEVICES

This application is a continuation of application Ser. No. 08/036,199 filed Mar. 23, 1993, now abandoned.

BACKGROUND OF THE INVENTION

The present invention relates to a method of inspecting particles that is desirable for fine pattern processing of semiconductor devices such as very large scale integrated circuits (VLSI) and the like.

In recent years, the extent of fineness in pattern processing of such semiconductor devices as VLSI, etc. has been consistently increasing. As the degree of the fineness progresses, the existence of particles such as very small dust particles has affected the yield rates of semiconductor devices.

According to the conventional method, the existence of particles has been examined by irradiating a laser light on a wafer surface and by detecting diffuse light beams which are scattered by particles attached to the wafer surface.

FIG. 6 illustrates how a conventional laser particle inspection apparatus works. A substrate to be inspected 30 is placed on a stage 31. An incident laser light beam 33 from a laser light source 32 is scattered by a particle 34 situated on the substrate to be inspected 30 to throw a diffuse light beam 35. This diffuse light beam 35 is inspected by a light detector 36. The stage 31 is driven into motion by a motor 37. The driving system, the laser source 32 and a light detector 36 are controlled by a controller 38 and the data outputted from the inspection apparatus are processed by a computer 39.

The locations of particles are accurately detected by synchronizing signals for the wafer rotation with signals from the light detector 36. However, it is difficult for the foregoing conventional set-up to detect particles of less than 0.1 μm in dimension because the intensity of the diffuse light beams is too weak to detect.

SUMMARY OF THE INVENTION

Liquid (e.g. water) drops are condensed on the wafer surface and diffuse light patterns scattered by the liquid drops are detected to find the distribution and dimensions of the particles attached to the wafer surface.

According to this method, a measurement of the distribution and dimensions of particles including ones of less than 0.1 μm in dimension can be performed due to the increased intensity of the diffuse lights. As a result, the yield rate of semiconductor devices is much improved.

DETAILED DESCRIPTION OF THE INVENTION

Figure 1:
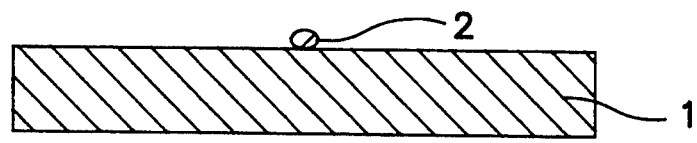
FIGS. 1 to 3 are cross-sectional illustrations for explaining a method of inspecting particles in accordance with an exemplary embodiment of the present invention.
Figure 2:
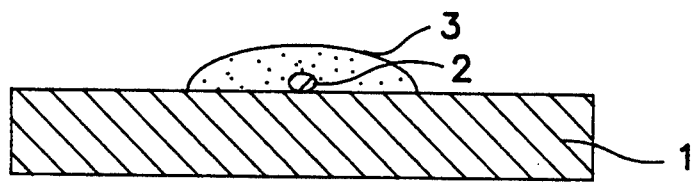
Figure 3:
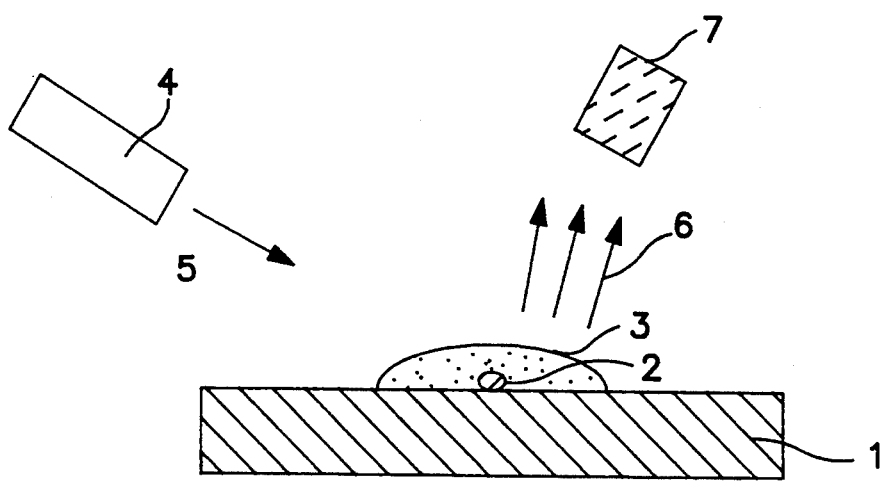

A particle inspection method in accordance with an exemplary embodiment of the present invention is explained in the following with the help of drawings:

FIGS. 1 to 3 are cross-sectional illustrations for explaining a method of inspecting particles in accordance with an exemplary embodiment of the present invention.

In FIG. 1, item 1 is a silicon substrate and item 2 is a particle attached to the silicon substrate. A water drop 3 was formed around the particle 2 by cooling the silicon substrate 1 down to temperatures ranging from −5° C. to +5° C. of the water condensation temperature. As shown in FIG. 3, a laser light beam 5 from a laser light source 4 was irradiated on the silicon substrate 1 and a diffuse light pattern 6 scattered by the water drop 3 was detected by a light detector 7. When the particle size was less than 0.1 μm, it was difficult for the light detector used in the conventional method to detect light for the reason that the diffuse light intensity was too weak. In contrast, according to the method of the present invention, the image of the particle 2 was magnified by the water drop 3 and the diffuse light pattern 6 was reflected with very high efficiency for detection by the light detector 7.

Figure 4:
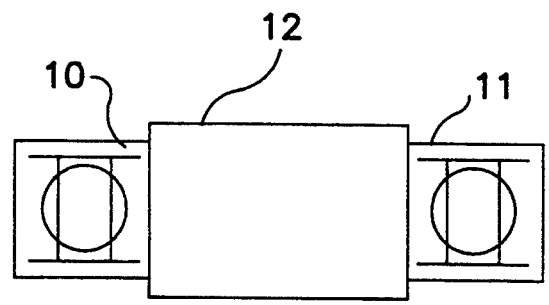
FIG. 4 shows a laser particle inspection apparatus which utilizes a method of inspecting particles in accordance with an exemplary embodiment of the present invention.
Figure 5:
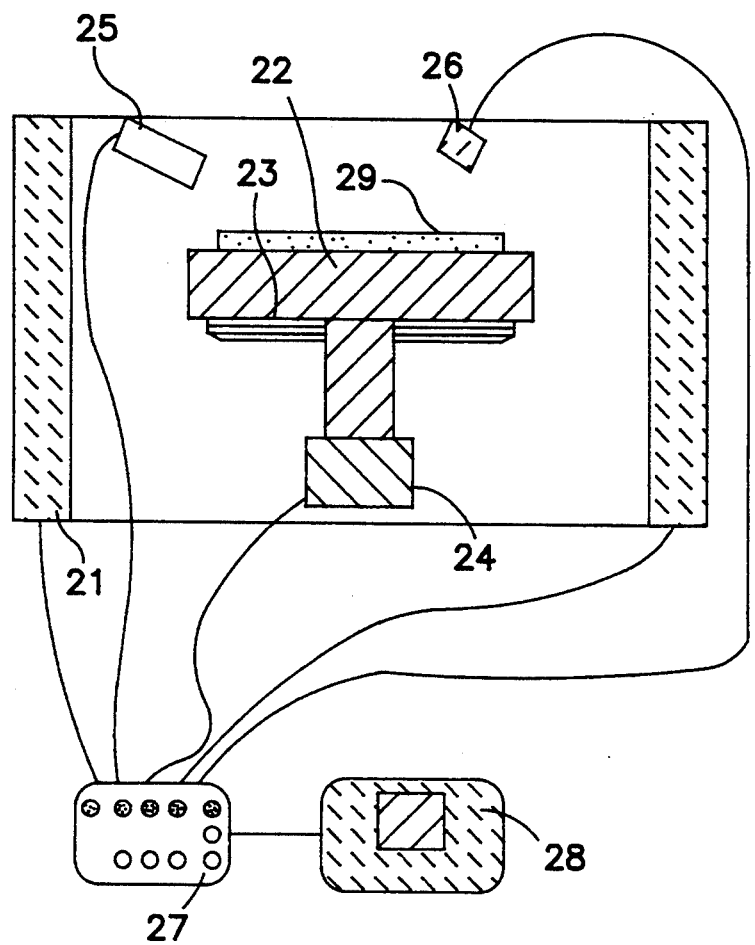
FIG. 5 is a detailed illustration of an inspection chamber which is included in the inspection apparatus of FIG. 4.
Figure 6:
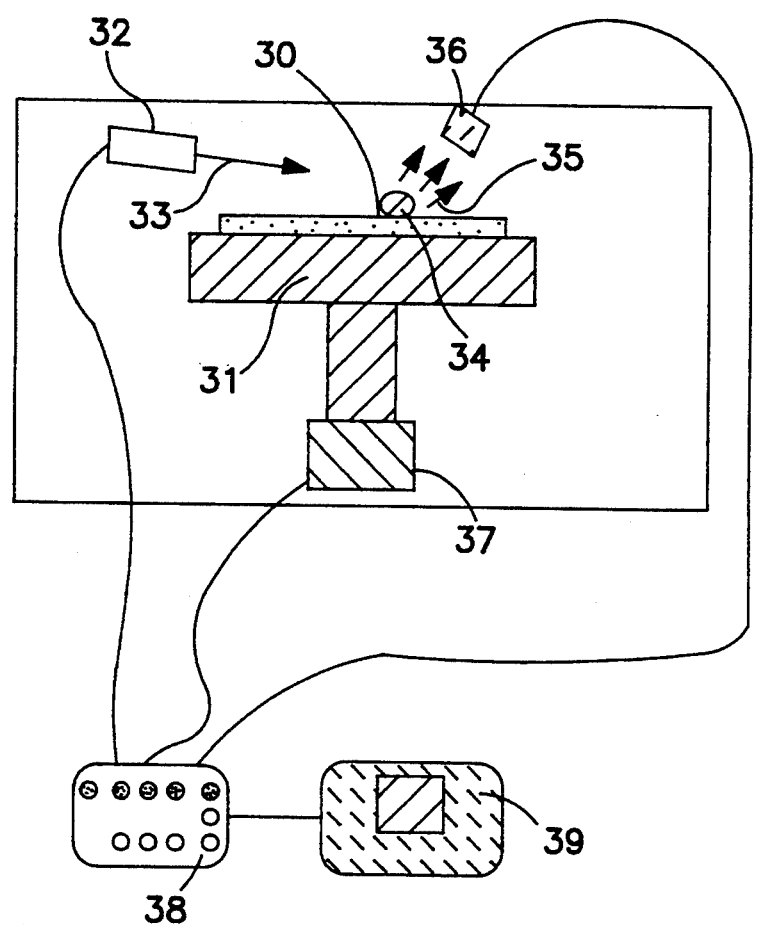
FIG. 6 is an illustration to describe the conventional method of particle inspection.

FIG. 4 shows a laser particle inspection apparatus which is in accordance with an exemplary embodiment of the present invention and composed of a loader 10, an unloader 11 and an inspection chamber 12. As shown in FIG. 5, the inspection chamber consists of an air conditioner 21 to maintain the chamber humidity at a high degree of humidity, a stage 22 to hold a substrate and a cooler 23 to lower the temperature of the stage to a certain degree of temperature. The humidity of the inspection chamber is kept at a higher level (around 70%) than that of the ambient (around 50%). Water drops are formed around particles on the substrate which has been cooled down to near the moisture condensation temperature by the cooler 23. The stage 22 is linked with a motor 24. As illustrated in FIG. 5, a laser light source 25 and a light detector 26 are installed in the inspection chamber, the motor 24, the laser light source 25 and the light detector 26 are controlled by the controller 27 and data processing, data displaying and the like are performed by a computer 28. Laser light beams irradiated from the laser light source 25 hit the substrate to be inspected 29 and the irregular reflection light patterns reflected therefrom are detected by the light detector 26.

The same effects can be obtained by drops made from any other vapors such as alcohol, for example, instead of water vapor. Besides, the inspection chamber need not necessarily be a closed vessel so long as the ambient temperature and humidity of the inspection apparatus are kept constant.

Although particles were detected by means of laser diffuse light beams in the foregoing example, a distribution of particles can be easily seen by diffuse light patterns resulting from slantingly irradiated light beams provided water drops are sufficiently grown.

In addition, the way the water drops are formed differs by the surface conditions, whether water repellent or hydrophobic. Therefore, this method can also be used to detect differences of surface conditions.

Further, by combining the particle inspection method utilizing diffuse light beams from the particles not surrounded by water drops and the inspection method of the exemplary embodiment of the present invention, a combined distribution of large size (0.1 μm and up in diameter) particles and small size (less than 0.1 μm in diameter) particles can be obtained accurately. In this case, the present invention's exemplary method of water drops condensed around particles can be applied either before or after the other method of using no water drops.

All in all, the present invention makes it possible to have more intensified diffuse laser light patterns from particles attached to a surface of a substrate to be inspected with water drops formed around the particles than from particles with no water drops surrounding them. As a result, particles of less than 0.1 μm in dimension are readily detected.

What is claimed:

1. A method of inspecting a plurality of particles on a surface of a substrate comprising:
   condensing a liquid drop only around each of said particles, said plurality of particles occupying only a portion of said surface of said substrate; and
   automatically detecting and examining a plurality of diffuse light patterns scattered by each liquid drop to automatically locate said plurality of particles and determining their size.

2. A method of inspecting a plurality of particles according to claim 1, wherein condensing each liquid drop around each particle on said surface of said substrate is performed with the substrate maintained at a temperature lower than ambient temperature to thereby have each liquid drop condensed only around each said particle on said substrate.

3. A method of inspecting a plurality of particles according to claim 1, wherein condensing each liquid drop on said surface of said substrate is performed in an atmosphere surrounding the substrate which has a humidity higher than ambient humidity and is performed with said substrate maintained at a temperature lower than that of the atmosphere to thereby have each liquid drop condensed only around each said particle located on said substrate.

4. A method of inspecting a plurality of particles according to claim 1, further including the step of irradiating laser light beams on the substrate.

5. A method of inspecting a plurality of particles according to claim 2, further including the step of irradiating laser light beams on the substrate.

6. A method of inspecting a plurality of particles according to claim 3, further including the step of irradiating laser light beams on the substrate.

7. A method of inspecting a surface of a substrate comprising:
   condensing a liquid drop only around each of a plurality of particles, said particles occupying only a portion of said surface of said substrate;
   automatically detecting and determining size of small particles included within said plurality of particles by analyzing diffuse light patterns scattered from each liquid drop, each of said small particles being attached to a portion of the surface of said substrate;
   removing each liquid drop from the surface of said substrate;
   irradiating a plurality of laser light beams on the surface of the substrate after each liquid drop has been removed; and
   automatically detecting and determining size of large particles included within said plurality of particles, each said large particle being attached only to a portion of said substrate surface, said detection being performed from an analysis of a plurality of light patterns scattered by said large particles, when said laser light beams are irradiated on the surface of said substrate.

8. A method of inspecting a surface of a substrate comprising:
   irradiating laser light beams on the surface of the substrate;
   automatically detecting and determining size of large particles included within a plurality of particles attached to the surface of the substrate, said detection occurring from an analysis of light patterns scattered by said large particles;
   condensing a liquid drop around each small particle within said plurality of particles, each small particle occupying only a portion of the surface of the substrate; and
   automatically detecting and determining size of each small particle attached to a portion of the surface of the substrate by analyzing diffuse lights scattered from each liquid drop.

9. A method of inspecting a plurality of particles on a surface of a substrate comprising:
   exposing said substrate to vapors of an alcohol;
   cooling said substrate to a temperature at which said alcohol vapor will condense on said substrate;
   condensing said alcohol vapor to form a drop of alcohol around said plurality of particles, said particles occupying only a portion of said surface of said substrate; and
   automatically detecting and determining size of said particles attached to a portion of said substrate surface by analyzing a plurality of diffuse light patterns scattered from the condensed alcohol vapor when laser beams are irradiated onto the substrate.

10. A method of inspecting a surface of a substrate comprising:
    exposing said substrate to an atmosphere containing water vapor;
    cooling said substrate to a temperature of within ±5° C. at which said water vapor will condense on said substrate;
    condensing a drop of water around particles located on a portion of the surface of the substrate to be inspected; and
    automatically detecting diffuse light beams scattered by each drop of water to determine surface conditions and size of said particles on said substrate.

11. A laser particle inspection apparatus comprising:
    an inspection chamber including a stage on which a substrate to be inspected is placed;
    a laser light source for irradiating laser light beams on said substrate to be inspected;
    light detection means for detecting diffuse light beams scattered by liquid drops surrounding small particles situated on a portion of said substrate to be inspected;
    means for cooling said stage; and
    means for forming a high humidity atmosphere around said substrate to be inspected so that the liquid drops are formed only around each small particle on said substrate.

12. A method according to claim 9 wherein said step of automatically detecting and determining size of said particles includes particles having a dimension less than 0.1 μm.

* * * * *